United States Patent
Tizabi

(10) Patent No.: US 12,168,035 B2
(45) Date of Patent: *Dec. 17, 2024

(54) C-TERMINAL FRAGMENT OF TETANUS TOXIN (HC) FOR TREATMENT OF DEPRESSION

(71) Applicant: HOWARD UNIVERSITY, Washington, DC (US)

(72) Inventor: Yousef Tizabi, Silver Spring, MD (US)

(73) Assignee: Howard University, Washington, DC (US)

( * ) Notice: Subject to any disclaimer, the term of this patent is extended or adjusted under 35 U.S.C. 154(b) by 187 days.

This patent is subject to a terminal disclaimer.

(21) Appl. No.: 17/729,502

(22) Filed: Apr. 26, 2022

(65) Prior Publication Data

US 2022/0249602 A1    Aug. 11, 2022

Related U.S. Application Data

(62) Division of application No. 16/878,809, filed on May 20, 2020, now Pat. No. 11,338,016.

(51) Int. Cl.
*A61K 38/16*    (2006.01)
*A61K 9/00*    (2006.01)

(52) U.S. Cl.
CPC .......... *A61K 38/164* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 11,338,016 B2 * | 5/2022 | Tizabi | .................. A61K 38/164 |
| 2002/0177545 A1 | 11/2002 | Donovan | |
| 2011/0263827 A1 | 10/2011 | Ghayur et al. | |

FOREIGN PATENT DOCUMENTS

WO    2007082973 A1    7/2007

OTHER PUBLICATIONS

Getachew et al. Antidepressant effects of C-Terminal domain of the heavy chain of tetanus toxin in a rat model of depression. Behavioral Brain Research 370 (May 22, 2019 Online) 111968, pp. 1-5.*
International Search Report issued Jul. 27, 2021 in International Application No. PCT/US2021/032370.
Written Opinion of the International Searching Authority issued Jul. 27, 2021 in International Application No. PCT/US2021/032370.

* cited by examiner

*Primary Examiner* — Maury A Audet
(74) *Attorney, Agent, or Firm* — Sughrue Mion, PLLC

(57) ABSTRACT

C-terminal domain of the heavy chain of tetanus toxin (Hc-TeTx) provides therapeutic effects in motor impairments associated with Parkinson disease (PD), and provides long lasting antidepressant effects, thus useful in treating and mitigating depression, particularly PD-depression co-morbid condition. A method for treating or mitigating depression, including administrating an effective amount of C-terminal domain of the heavy chain of tetanus toxin (Hc-TeTx) to a subject in need thereof. A method for treating or mitigating motor impairments associated with Parkinson's disease (PD), including administrating an effective amount of C-terminal domain of the heavy chain of tetanus toxin (Hc-TeTx) to a subject in need thereof.

4 Claims, 2 Drawing Sheets

C-TERMINAL FRAGMENT OF TETANUS TOXIN (HC) FOR TREATMENT OF DEPRESSION

This is a divisional of application Ser. No. 16/878,809 filed May 20, 2020, the entire contents thereof are incorporated herein by reference.

STATEMENT REGARDING FEDERALLY SPONSORED RESEARCH OR DEVELOPMENT

Some aspects of this invention were made in the course of Grant NIH/NIAAA R03AA022479 awarded by the National Institutes of Health and therefore the Government has certain rights in some aspects of this invention.

TECHNICAL FIELD

Methods pertain to treatment or mitigation of depression, particularly depression-Parkinson's disease (PD) co-morbid condition. Particularly, methods comprise administering Carboxyl-terminal domain of the heavy chain of tetanus toxin (Hc-TeTx) or any atoxic fraction of the tetanus toxin or the coding sequence of the Hc-TeTx in treatment or mitigation of depression.

BACKGROUND

The toll extracted by clinical depression, characterized by a despondent feeling, loss of interest in pleasurable activities, guilt, worthlessness, and trouble concentrating, is of immense medical concern. This is because the prevalence is relatively high. In the U.S. alone, approximately 16 million people or 7% of the adults are afflicted with major depressive disorder, which may also include abnormalities in appetite and sleep and loss of productivity and suicidal ideation. The actual suicide rate, estimated at 1 million worldwide, not only affects the afflicted individual but also the family and friends and at times the entire community (P. E. Greenberg, A. A. Fournier, T. Sisitsky, et al., The economic burden of adults with major depressive disorder in the United States, (2005 and 2010) J Clin Psychiatry, 76 (2015), pp. 155-162).

Although our understanding of the highly complex neurobiological circuitry of mood regulation remains far from complete, it is known that the symptoms of depression are diverse and vary from patient to patient. In addition, a number of drugs developed over the past six decades such as, tricyclic antidepressants (TCAs), monoamine oxidase inhibitors (MAOIs), norepinephrine reuptake inhibitors (NRIs), and selective serotonin reuptake inhibitors (SSRIs) have offered significant relief to at least some of the patients (M. R. Levinstein, B. A. Samuels, Mechanisms underlying the antidepressant response and treatment resistance, Front Behav Neurosci, 8 (2014), pp. 208). These medications, however, based on biogenic amine theory of depression, which posits that a decrease in these neurotransmitters is the primary cause of the disorder, have several major drawbacks. These include: limited efficacy, delayed onset and various undesirable side effects, some of which may be persistent (A. J. Rush, Targeting treatments for depression: what can our patients tell us? Epidemiol. Psychiatr Sci, 26 (2017), pp. 37-39; J. Ben-Sheetrit, D. Aizenberg, A. B. Csoka, et al., Post-SSRI sexual dysfunction: clinical characterization and preliminary assessment of contributory factors and dose-response relationship. J Clin Psychopharmacol, 35 (2015), pp. 273-278). Hence more rapid onset antidepressants with wider efficacy and lower side effects are urgently needed.

Recent elucidation of significant contribution of neurotrophic factors and inflammatory processes in mood regulation/dysregulation, has pointed new approaches in development of more effective antidepressants. In this regard, several natural and synthetic compounds with anti-inflammatory properties and ability to increase neurotrophic factors, particularly brain-derived neurotrophic factor (BDNF) have been proposed as potential novel antidepressants (L. L. Hurley, Y. Tizabi, Neuroinflammation, neurodegeneration, and depression. Neurotox. Res, 23 (2013), pp. 131-144; O. Kalejaiye, B. Getachew, C. L. Ferguson, et al., Alcohol-Induced Increases in Inflammatory Cytokines Are Attenuated by Nicotine in Region-Selective Manner in Male Rats. J Drug Alcohol Res, (2017), pp. 6: 236036; C. N. Bodnar, J. M. Morganti, A. D. Bachstetter, Depression following a traumatic brain injury: uncovering cytokine dysregulation as a pathogenic mechanism. Neural Regen Res., 13 (2018), pp. 1693-1704; R. S. Duman, BDNF, 5-HT, and anxiety: identification of a critical periadolescent developmental period. Am. J. Psychiatry, 174 (2017), pp. 1137-1139). However, no study on the C-terminal domain of the heavy chain of tetanus toxin (Hc-TeTx) as a potential antidepressant has been conducted.

SUMMARY OF THE INVENTION

The present inventors have conducted an extensive research and have discovered that the C-terminal domain of the heavy chain of tetanus toxin (Hc-TeTx) has antidepressant effects in an animal model of depression and can be effective in treating depression, particularly depression associated with Parkinson's disease (PD). The present inventors have discovered that Hc-TeTx resulted in a dose-dependent decrease in immobility score, whereas the open field locomotor activity (OFLA) was not affected. Concomitant with the behavioral effects, the inventors have discovered an increase in central brain-derived neurotrophic factor (BDNF) but a decrease in tumor necrosis factor (TNF)-alpha (TNF-alpha) in the hippocampus and the frontal cortex, two areas intimately associated with mood regulation (J. Jin and S. Maren, Prefrontal-hippocampal interactions in memory and emotion. Frontiers Systems Neuroscience, 9 (2015), pp. e170; Getachew, S. R. Hauser, A. B. Csoka et al., Role of cortical alpha-2 adrenoceptors in alcohol withdrawal-induced depression and tricyclic antidepressants. Drug Alcohol Depend., 175 (2017), pp. 133-139). These results indicate long lasting antidepressant effects of Hc-TeTx and suggest potential utility of Hc-TeTx in depression, particularly PD-depression co-morbidity.

Characteristics described above, other characteristics, and advantages of the invention are clearly revealed with reference to the descriptions below and accompanying drawings.

DETAILED DESCRIPTION OF THE INVENTION

Figure 1:
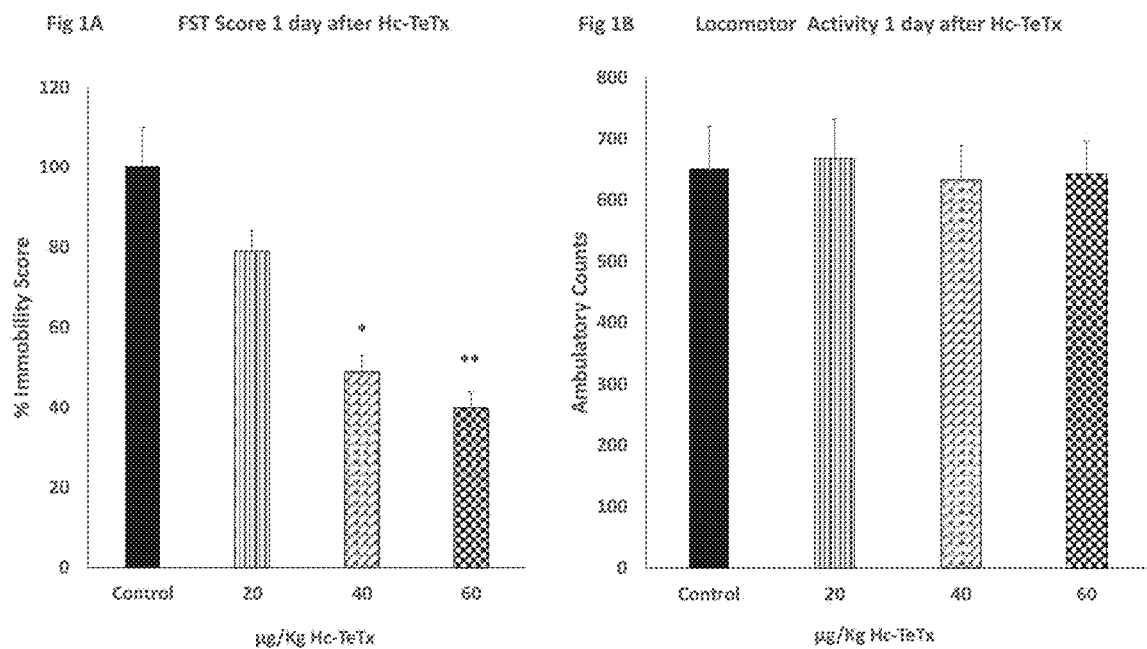
FIG. 1 shows effects of various doses of Hc-TeTx on immobility in the forced swim test (1A) and open field locomotor activity (1B) in WKY rats. The animals were tested 24 h after the single i.m. injection. Values are mean±SEM. N=6/group. *$p<0.05$, **$p<0.01$ compared to control.

Tetanus toxin is a synthesized single peptide of approximately 150 kDa, which consists of 1315 amino-acid residues. An endogen clostrial protease forms a two-chain activated molecule composed of a heavy chain (HC) and a light chain (LC) linked by a disulfide bond. The catalytic domain of the toxin resides in the LC, while the translocation and receptor-binding domains are present in HC. The C-terminal domain of heavy chain of tetanus toxin (Hc-TeTx) is a nontoxic fragment of TeTx with demonstrated capacity to protect against cell death induced by a variety of neurotoxins including methamphetamine (I. Chaib-Oukadour, C. Gil, J. Rodriguez-Alvarez, et al., Tetanus toxin H(C) fragment reduces neuronal MPP+ toxicity. Mol Cell Neurosci, 41 (2009), pp. 297-303; L. Mendieta, B. Venegas, N. Moreno, et al., The carboxyl-terminal domain of the heavy chain of tetanus toxin prevents dopaminergic degeneration and improves motor behavior in rats with striatal MPP(+)-lesions. Neurosci Res 65 (2009), pp. 98-106; A. Sanchez-Gonzalez, L. Mendieta, V. Palafox, et al., The restorative effect of intramuscular injection of tetanus toxin C-fragment in hemiparkinsonian rats. Neurosci Res, 84 (2014), pp. 1-9.L; Mendieta, N. Granado, J. Aguilera, et al., Fragment C domain of tetanus toxin mitigates methamphetamine neurotoxicity and its motor consequences in mice. Int J Neuropsychopharmacol, 19 (2016), pyw021; L. Radenovic, V. Selakovic, S. Olivan, et al., Neuroprotective efficiency of tetanus toxin C fragment in model of global cerebral ischemia in Mongolian gerbils. Brain Res Bull, 101 (2010), pp. 37-44; M. C. Sozbilen, M. Ozturk, G. Kaftan, et al., Neuroprotective effects of C-terminal domain of tetanus toxin on rat brain against motorneuron damages after experimental spinal cord injury. Spine, (Phila Pa 1976) 43 (2018), pp. E327-E333). A strong association between neurodegenerative diseases (e.g. PD) and neuropsychiatric disorders (e.g. depression) in terms of neurobiological substrates as well as drug treatment has been indicated (Y. Tizabi, Duality of Antidepressants and Neuroprotectants. Neurotox Res, 30 (2016), pp. 1-13).

The present inventors have undertaken, for the first time, the study to investigate the potential antidepressant effects of Hc-TeTx in an animal model of depression. The present inventors have discovered that Hc-TeTx resulted in a dose-dependent decrease in immobility score, whereas the open field locomotor activity (OFLA) was not affected Immobility in the forced swim test (FST) is a measure of helplessness or depressive-like behavior (W. P. Pare, Open field, learned helplessness, conditioned defensive burying, and forced-swim tests in WKY rats. Physiol Behav, 55 (1994), pp. 433-439). Concomitant with the behavioral effects, the inventors have discovered an increase in central brain-derived neurotrophic factor (BDNF) but a decrease in tumor necrosis factor (TNF)-alpha (TNF-alpha) in the hippocampus and the frontal cortex, two areas intimately associated with mood. These results indicate long lasting antidepressant effects of Hc-TeTx and suggest potential utility of Hc-TeTx in depression, particularly PD-depression co-morbidity.

One example embodiment of the disclosed subject matter provides an agent for depression treatment or mitigation, containing C-terminal domain of the heavy chain of tetanus toxin (Hc-TeTx) as an active ingredient.

Another example embodiment of the disclosed subject matter provides a method for treating or mitigating depression, comprising administering an effective amount of Hc-TeTx to a patient in need thereof.

In one of its aspects, the depression is depression associated with Parkinson's disease (PD) or PD-Depression co-morbidity.

In one of its aspects, Hc-TeTx increases central brain-derived neurotrophic factor (BDNF) in the hippocampus and the frontal cortex.

In one of its aspects, Hc-TeTx decreases tumor necrosis factor (TNF)-alpha (TNF-alpha) in the hippocampus and the frontal cortex.

In one of its aspect, Hc-TeTx has long lasting effect, which would allow for less frequent administration of the drug.

The formulation of Hc-TeTx and method of administration of Hc-TeTx can be selected suitably. For example, the Hc-TeTx can be formulated in a liquid suitable for administration by injection or by nasal spray. This formulation can be produced by well-known methods.

The injection or nasal spray agents include solutions of solid agents to be dissolved in a solvent before use. The injection or nasal spray agent is used by, for example, dissolving an active ingredient in a solvent. Examples of the solvent include distilled water for injection, physiological saline, etc. Furthermore, the injection or nasal spray agent may contain a stabilizer, a dissolution aid, a suspending agent, an emulsifying agent, a soothing agent, a buffer, a preservative, and the like. Such an injection agent is produced by sterilizing at the final step or employing an aseptic process.

The dose of the Hc-TeTx to be used is different depending on ages, body weights, symptoms, therapeutic effects, administration method, treatment time, and the like. For example, the dose of the Hc-TeTx per adult is generally from 150 µg to 600 µg per dose, in one aspect from 180 µg to 540 µg per dose, and in another aspect from 180 µg to 360 µg per dose, once every two weeks by parenteral administration (most likely intramuscular or it could be applied by a single intranasal dose). Needless to say, as mentioned above, the dose to be used varies dependent on various conditions. Therefore, the lowest dose specified above may be sufficient in some cases, and a dose higher than the range specified above may be needed in some cases.

The Hc-TeTx may be administered in combination with other medicine (for example, well-known agents for depression treatment) for the purposes of: (1) supplementing and/or enhancing therapeutic effect, (2) improving the kinetics, improving absorption, and reducing the dose; and/or (3) eliminating the adverse reaction of the compound.

EXAMPLES

The present invention is explained below in further detail with reference to Examples. However, the scope of the invention is not limited to these Examples.

Wistar Kyoto (WKY) rats, an inbred strain, initially developed as a normotensive control for the spontaneously hypertensive rats, were later found to demonstrate exaggerated immobility in the forced swim test (FST), a measure of helplessness or depressive-like behavior (W. P. Pare, Open field, learned helplessness, conditioned defensive burying, and forced-swim tests in WKY rats. Physiol Behav, 55 (1994), pp. 433-439). Moreover, it was found that these rats are irresponsive to selective serotonin reuptake inhibitors (SSRIs), and hence may be considered as a model of treatment resistant depression (C. Lopez-Rubalcava, I. Lucki, Strain-dependent modification of behavior following antidepressant treatment. Prog Neuropsychopharmacol Biol Psychiatry, 27 (2003), pp. 7-14; C. C. Will, E. E. Aird, F., Redei, selectively bred Wistar-Kyoto rats: an animal model of depression and hyper-responsiveness to antidepressants. Mol Psychiatry, 8 (2003), pp. 925-932).

Adult male WKY rats, 14-15 weeks old and weighing about 250 g, were obtained from Envigo (previously Harlan Laboratories, Indianapolis, IN). Animals receiving the same treatment were pair-housed through the duration of the experiment in a standard polypropylene shoebox cages (42×20.5×20 cm) on chip bedding. Animals were subjected to a 1-week acclimatization period upon their arrival, during which they were handled daily to minimize any handling related stress. Throughout the study, with the exception of behavioral tests, animals had free access to food (Harlan Tek Lab) and water. The room was maintained at 24-26° C. at 55-66% relative humidity, on a reverse light cycle (lights on 7:00 PM-7:00 AM) to allow convenient behavioral evaluations of the animals during their active period. Acclimatization to reversed dark cycle was done over a one-week period where the light hours were shifted by approximately 2 h daily. All behavioral testing and injections occurred between 8:00 A.M. and 12:00 P.M. during the animal's active phase. All experiments were carried out in accordance with NIH guidelines, as approved by the Institutional Animal Care and Use Committee of the Howard University.

Animals were divided into three groups (n=6/group) and received intramuscular (i.m.) injection of either saline (control) or 20, 40, or 60 µg/kg dose of Hc-TeTx. The injection was into the gastrocnemius muscle. Hc-TeTx fragment was synthesized as described in detail previously (Hernando-Grabulosa M, Casas C, Aguilera J. The C-terminal domain of tetanus toxin protects motoneurons against acute excitotoxic damage on spinal cord organotypic cultures. *J Neurochem.* 2013; 124(1):36-44) and indicated below.

Hc-TeTx Purification

*Escherichia coli* BL21 cells were transformed with pQE3 (Qiagen, Chatsworth, CA, USA) vector encoding for (6×His)-tagged Hc-TeTx and were grown in Luria Bertani medium containing 100 μg/mL ampicillin as reported previously (Gil C., Chaib-Oukadour I. and Aguilera J. (2003) C-terminal fragment of tetanus toxin heavy chain activates Akt and MEK/ERK signaling pathways in a Trk receptor-dependent manner in cultured cortical neurons. *Biochem. J.* 373, 613-620). Protein expression was induced by the addition of 0.4 mM isopropyl β-D-thiogalactoside (IPTG). After 3 h, cells were pelleted by centrifugation at 4000 g for 20 min at 4° C., re-suspended in lysis buffer (50 mM $NaH_2PO_4$, 300 mM NaCl, and 1% Triton-X-100; pH 8) and sonicated on ice for six 30 s periods. The suspension was centrifuged at 30000 g for 30 min at 4° C. The clear supernatant, which contains the His-tagged protein, was purified by cobalt affinity chromatography. Mixed proteins were injected in a Fast Protein Liquid Chromatography (FPLC), which contains a cobalt-agarose resin (TALON Metal Affinity resin; Clontech Laboratories, Palo Alto, CA, USA), previously equilibrated (50 mM $NaH_2PO_4 \cdot H_2O$ and 300 mM NaCl; pH 7). The proteins, without His-Tags, were eluted by washing the resin with elution buffer (50 mM $NaH_2PO_4 \cdot H_2O$ and 300 mM NaCl; pH 7). Hc-TeTx contains six histidines, which is retained in the resin forming a Co-complex. Hc-TeTx was eluted with the elution buffer (50 mM $NaH_2PO_4 \cdot H_2O$, 300 mM NaCl and 150 mM Imidazole; pH 7). Fractions collected were 0.5 mL volume. The elution process can be followed with FPLC system, that measures the absorbance at 280 nm constantly. Protein was separated by sodium dodecyl sulfate-polyacrylamide gel electrophoresis (SDS-PAGE) at 12%. Gel was stained with GelCode Blue Stain Reagent (Pierce Chemical Co., Rockford, IL, USA) and those tractions containing purified Hc-TeTx protein were dialyzed (40 mM $Na_7HPO_4$, 10 mM $NaH_2PO_4$ and 150 mM NaCl; pH 7.4), overnight at 4° C., and for 2 h with new buffer. Protein concentrations were determined using the bicinchoninic acid assay (BCA; Pierce Chemical Co.) and lyophilized. The Hc-TeTx was stored in aliquots at −20° C.

In addition, to determine the absorption and uptake and subsequent arrival at the spinal cord level, Alexa Fluor®555 was attached to Hc-TeTx following the manufacturer's protocol from Alexa Fluor®555 Labeling Kit (Invitrogen, Carlsbad, CA, USA) and stored at −20° C.

The Hc-TeTx solution was prepared by dissolving 1 mg of lyophilized Hc-TeTx in 1 mL of isotonic saline solution (0.9% HCl), followed by serial dilutions to obtain a final concentration of 20, 40 or 60 μg/100 The volume of injection was 400 μL/kg. Hence each animal received approximately 100 μL of saline or the drug.

Approximately 24 h after the last injection, animals were tested in an open-field activity monitoring cage (27×27×20.3 cm, Med Associates, Inc., St. Albans, VT) for 5 min where ambulatory counts representing the number of infrared beam interruptions were recorded. This behavior was assessed to determine if drug treatment affected general locomotor behavior, which might impinge on forced swim test immobility assessment (L. Akinfiresoye, Y. Tizabi, Antidepressant effects of AMPA and ketamine combination: role of hippocampal BDNF, synapsin, and mTOR. Psychopharmacology (Berl), 230 (2013), pp. 291-298; B. Getachew, Y. Tizabi, Both ketamine and NBQX attenuate alcohol-withdrawal induced depression in male rats. J Drug Alc Res, 8 (2019), pp. 1-7).

Immediately following the open field activity test each animal was evaluated for its behavior (immobility) in Forced Swimming Test (FST). Briefly, each rat was placed in a Pyrex cylinder pool measuring 17 cm in diameter and 60 cm in height for 5 min. The cylinder was filled with 30 cm water (25±1° C.) to ensure that the animals could not touch the bottom of the container with their hind paws or their tails. The FST activity was video recorded for subsequent analysis. The rat was removed after 5 min, dried, and placed in its home cage. A time sampling scoring technique was used whereby the predominant behavior in each 5-s period of the 300-s test was recorded. Inactivity (immobility) and activity (swimming) were distinguished as mutually exclusive behavioral states. Swimming behavior was defined as movement (usually horizontal) throughout the cylinder Immobility was defined when no additional activity was observed other than that required to keep the rat's head above the water.

Since behavioral effects were observed a day after a single Hc-TeTx injection, both OFLA and FST were repeated after one week of rest and again after two weeks of rest to determine the lasting effects of the single drug injection on these parameters.

A separate group of rats were treated with the 60 µg/kg dose of Hc-TeTx as this dose had resulted in the highest behavioral (antidepressant) effect. Animals were sacrificed by decapitation, approximately 24 h later to coincide with the time of behavioral observation. No behavioral tests were done in these animals. This was to avoid potential confounding effects of swim test on neurochemical parameters. Brains were quickly removed, frozen on dry ice and stored at −80° C. until dissection for BDNF and TNF-alpha measurement. The hippocampus (bilateral) and frontal cortex were dissected as described (Tizabi Y, Getachew B, Rezvani A H, Hauser S R, Overstreet D H. Antidepressant-like effects of nicotine and reduced nicotinic receptor binding in the Fawn-Hooded rat, an animal model of co-morbid depression and alcoholism. *Prog Neuropsychopharmacol Biol Psychiatry.* 2009; 33 (3):398-402) and detailed below. Brains were thawed and kept on an ice-cold plate. Frontal cortex (up to the genu of corpus callosum and excluding the olfactory bulb and olfactory tubercle), and hippocampus (bilateral) were removed and stored frozen at −80° C. until assayed.

Western blot was performed as described in detail in the following two documents, the disclosures of which are incorporated herein by reference: B. Getachew, S. R. Hauser, A. B. Csoka et al., Role of cortical alpha-2 adrenoceptors in alcohol withdrawal-induced depression and tricyclic antidepressants. Drug Alcohol Depend., 175 (2017), pp. 133-139; and L. Akinfiresoye, Y. Tizabi, Antidepressant effects of AMPA and ketamine combination: role of hippocampal BDNF, synapsin, and mTOR. Psychopharmacology (Berl), 230 (2013), pp. 291-298). Briefly, homogenate of the dissected hippocampus (bilateral) were made in lysis buffer (10 mM Tris-buffer, 5 mM EDTA, 150 mM NaCl, 0.5% Triton X-100 (v/v) with protease inhibitors (Sigma-Aldrich, St. Louis, MO). The protein concentration in each sample was determined using a BCA protein Assay Kit (Pierce Biotechnology Inc., IL), and equal protein amount (as confirmed by β-actin) was loaded in each immunoblot. The proteins were separated using 12% SDS-PAGE gel and transferred onto a nitrocellulose membrane. The membranes were blocked with a blocking reagent (5% nonfat milk in TBS buffer) for ½ h and incubated at 4° C. overnight with the primary antibody against BDNF (1:500, Santa Cruz Biotechnology Inc., Santa Cruz, CA) or TNF-alpha (1:500, Santa Cruz Biotechnology). The membranes were washed with TBST (TBS buffer with 1% Tween-20) and blocked with the blocking reagent. Membranes were then incubated for 1 h at room temperature in Goat Anti-Rabbit-HRP conjugated secondary antibody (1:3000 in TBS, Bio-Rad Laboratories, CA). The membranes were then washed in the TBST washing solution and then visualized using enhanced chemiluminescent kits (Bio-Rad Laboratories, CA). The intensity of the protein bands on the gel was quantified using ChemiDoc XRS system (Bio-Rad Laboratories, CA).

Statistical differences between treatment groups were determined by one-way analysis of variance (ANOVA) followed by post-hoc Newman-Keuls Multiple comparison test to determine which groups differed. Significant difference was set a priori at $p<0.05$. Data were analyzed using Graphpad Prism6 (Graphpad Software, Inc., San Diego, CA, USA).

Single treatment with Hc-TeTx resulted in a dose-dependent decrease in FST immobility when tested 24 h after the injection $[F(3,28)=6.38, p<0.01]$. Thus, the 60 µg/kg dose caused the highest decrease (60% $p<0.01$), the 40 µg/kg (51% $p<0.01$) and the 20 µg/kg (21% $p<0.05$) in immobility compared to the control (FIG. 1A). Open field locomotor activity was not altered by any treatment (FIG. 1B), suggesting that the treatment effects of Hc-TeTx on FST were independent of any effects on general locomotion.

Based on these results, the present inventors used the highest dose of 60 µg/kg to evaluate the neurochemical changes associated with this behavioral effect.

Figure 2:
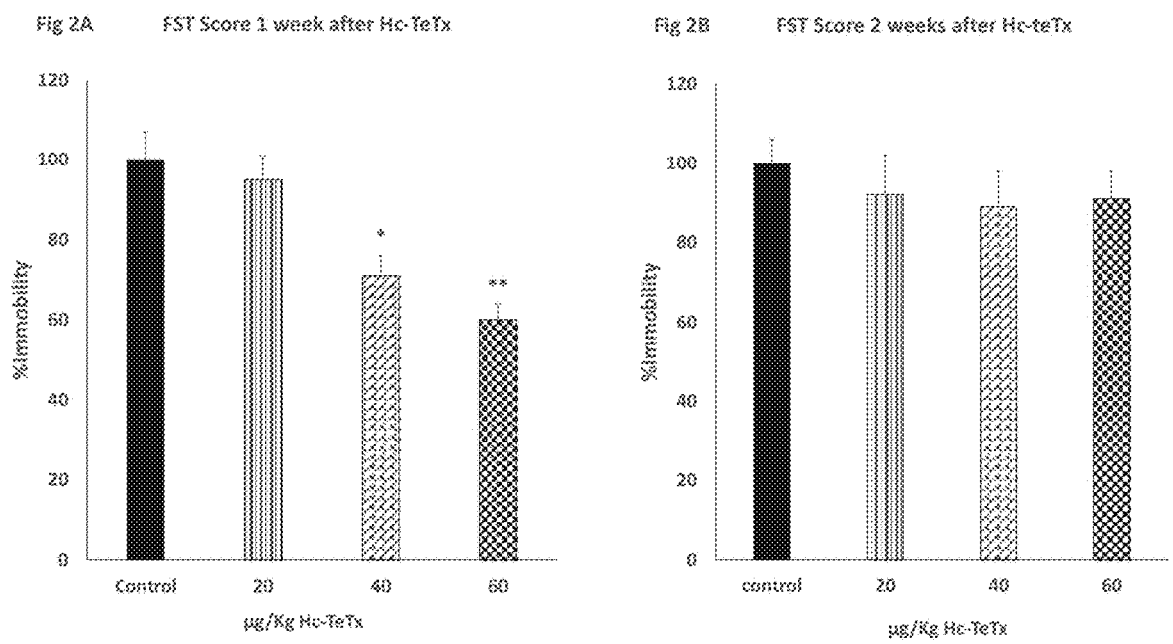
FIG. 2 shows effects of various doses of Hc-TeTx on immobility in the forced swim test in WKY rats. The animals were tested one week (2A) and two weeks (2B) after the single i.m. injection. Values are mean±SEM. N=6/group. *p<0.05, **p<0.01 compared to control.

One week after the last single injection, the effect of 40 and 60 µg/kg doses were still evident on immobility scores $[F(3,28)=5.96, p<0.01]$. Hence, with the 40 µg/kg dose, there was 29% decrease in immobility ($p<0.05$) and with 60 µg/kg dose, there was 39% decrease ($p<0.01$) (FIG. 2A). After 2 weeks of rest the effect of 40 µg/kg dose was totally absent (FIG. 2B). Although there was still a 13% decrease in immobility score after the 60 µg/kg dose, this effect was not statistically significant $[F(3,28)=0.68, p>0.64]$.

Figure 3:
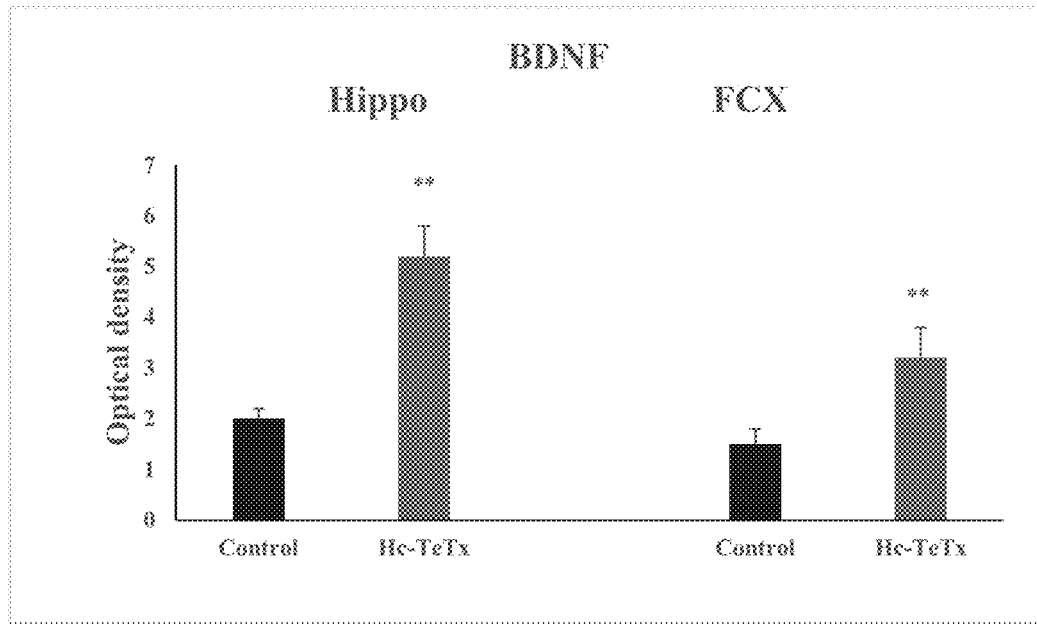
FIG. 3 shows effects of Hc-TeTx on BDNF levels in the hippocampus (Hippo) and the frontal cortex (FCX) of WKY rats treated with 60 µg/kg Hc-TeTx. The animals were sacrificed 24 h after the single i.m. injection of Hc-TeTx. Values are mean±SEM. N=6/group. **p<0.01 compared to control.
Figure 4:
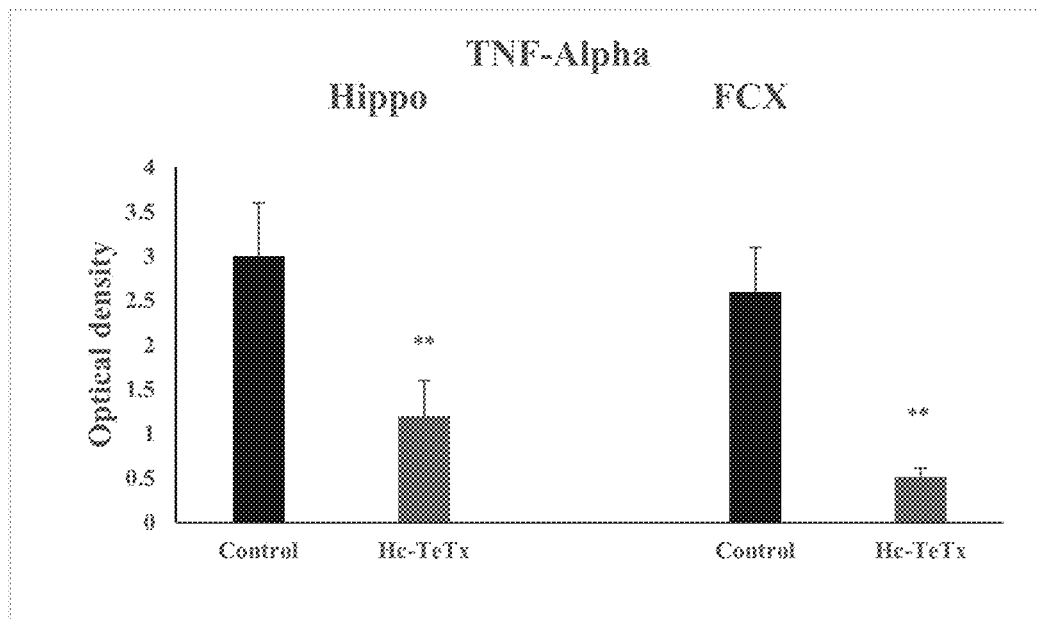
FIG. 4 shows effects of Hc-TeTx on TNF-alpha levels in the hippocampus (Hippo) and the frontal cortex (FCX) of WKY rats treated with 60 µg/kg Hc-TeTx. The animals were sacrificed 24 h after the single i.m. injection of Hc-TeTx. Values are mean±SEM. N=6/group. **p<0.01 compared to control.

Western blot analysis showed that acute treatment with the 60 µg/kg dose of Hc-TeTx resulted in increases in BDNF levels in the hippocampal (2.6-fold, $p<0.01$) and the frontal cortex (2.1-fold $p<0.01$) 24 h after a single administration (FIG. 3). An opposite trend was observed in terms of TNF-alpha levels in both areas. Hence, 60 µg/kg dose of Hc-TeTx resulted in decreases in TNF-alpha levels in the hippocampal (2.5-fold, $p<0.01$) and the frontal cortex (5-fold $p<0.01$) 24 h after a single administration (FIG. 4).

The results suggest antidepressant-like effects of an acute dose of Hc-TeTx in an animal model of treatment-resistant depression. This effect was long lasting as the behavioral despair reflected in the immobility scores of the FST was still down one week after the injection. Since potential utility of Hc-TeTx in movement disorders associated with PD has been verified by a number of preclinical studied (F. Patricio, I. Parra, I. Martinez, et al., Effectiveness of fragment C domain of tetanus toxin and pramipexole in an animal model of Parkinson's disease. Neurotox Res, 35 (2019), pp. 699-710; L. Mendieta, E. Bautista, A. Sanchez, et al., The C-terminal domain of the heavy chain of tetanus toxin given by intramuscular injection causes neuroprotection and improves the motor behavior in rats treated with 6-hydroxydopamine. Neurosci Res, 74 (2012), pp. 156-167) and co-morbidity of depression with PD is also well established (R. M. J. van der Velden, M. P. G. Broen, M. L. Kuijf, et al., Frequency of mood and anxiety fluctuations in Parkinson's disease patients with motor fluctuations: A systematic review. Mov Disord, 33 (2018), pp. 1521-1527), it may be concluded that Hc-TeTx would be of specific benefit in such co-morbid condition. This contention is further supported by the findings that neuroprotectants in general, are likely to have antidepressant effects as well (Y. Tizabi, Duality of Antidepressants and Neuroprotectants. Neurotox Res, 30 (2016), pp. 1-13).

The results also implicate a role for the neurotrophic factor, BDNF and at least one of the pro-inflammatory cytokines, TNF-alpha in antidepressant effects of Hc-TeTx. This is due to the fact the levels of the BDNF in both hippocampus and the frontal cortex were elevated by Hc-TeTx, whereas the levels of TNF-alpha were reduced in both these areas a day after the drug injection, concomitant with the observed antidepressant effects.

In summary, adult male Wistar-Kyoto rats, a putative animal model of depression, were treated with various doses of Hc-TeTx (0, 20, 40 and 60 µg/kg, IM) and their performance in the open field locomotor activity (OFLA) as well as in the forced swim test (FST) was evaluated at 24 h, one week and two weeks after the single injection. A separate group of rats were injected with 60 µg/kg Hc-TeTx and sacrificed 24 h later for neurochemical evaluations. Hc-TeTx resulted in a dose-dependent decrease in immobility score after 24 h, whereas OFLA was not affected. Concomitant with the 24 h behavioral effects, the levels of hippocampal and frontal cortical BDNF were significantly increased, whereas the levels of TNF-alpha in both these areas were significantly decreased. The decrease in immobility scores following higher doses of Hc-TeTx were still evident after one week, but not 2 weeks of rest. These results indicate long lasting antidepressant effects of a single Hc-TeTx dose and suggest potential utility of Hc-TeTx as a novel intervention in PD-depression co-morbid condition.

Although current approved antidepressants are primarily based on the monoaminergic hypothesis, which posits that a decrease in the levels of neurotransmitters such as norepinephrine, dopamine and serotonin (5HT) in the brain, is responsible for mood dysregulation, the delay in onset of action of such antidepressants and their limited efficacy has shifted the focus to other potential biological substrates. In this regard, a role for neurotrophic factors, particularly hippocampal and also frontal cortical BDNF and more recently, dysregulation of immune system, reflected in elevated levels of pro-inflammatory cytokines such as TNF-alpha have gained substantial traction in the field. Thus, it is now hypothesized that the delay in onset of action of current antidepressants might be due to the delay in elevation of the neurotrophic factors. Moreover, inhibition of both basal and stimulated serotonin uptakes in primary neuronal cultures were demonstrated by Hc-TeTx. Also, in-vivo studies show that Hc-TeTx increases the activity of tryptophan hydroxylase, a key enzyme in the synthesis of serotonin, which can lead to maintaining high levels of serotonin in the central nervous system.

While the subject matter disclosed herein has been described in connection with what is presently considered to be practical example embodiments, it is to be understood that the present disclosure is not limited to the disclosed embodiments, and covers various modifications and equivalent arrangements included within the spirit and scope of the appended claims.

What is claimed is:

1. A method for treating or mitigating depression in a patient having Parkinson's disease (PD), comprising administrating an effective amount of C-terminal domain of the heavy chain of tetanus toxin (Hc-TeTx) to a subject in need thereof.

2. The method according to claim 1, wherein the Hc-TeTx is administered by injection.

3. The method according to claim 1, wherein the Hc-TeTx is administered in an amount of 150 μg to 600 μg.

4. The method according to claim 1, wherein the Hc-TeTx is administered in an amount of 180 μg to 540 μg.

* * * * *